(12) United States Patent
Grum-Schwensen et al.

(10) Patent No.: US 9,949,865 B2
(45) Date of Patent: Apr. 24, 2018

(54) OSTOMY APPLIANCE COUPLING SYSTEM AND AN OSTOMY APPLIANCE

(75) Inventors: Christen Grum-Schwensen, Hillerød (DK); Ole Skjoedt, Rungsted Kyst (DK); Kasper Sortkjær, Hillerød (DK); Kenneth Nielsen, Ålsgårde (DK); Sussie Richmann, Hellebæk (DK); Peter Møller-Jensen, Hombæk (DK); Tue K. Toft, København (DK); Martin von Bülow, Helsingør (DK)

(73) Assignee: HOLLISTER INCORPORATED, Libertyville, IL (US)

( * ) Notice: Subject to any disclaimer, the term of this patent is extended or adjusted under 35 U.S.C. 154(b) by 1681 days.

(21) Appl. No.: 13/265,507

(22) PCT Filed: Apr. 27, 2010

(86) PCT No.: PCT/EP2010/055577
§ 371 (c)(1),
(2), (4) Date: Feb. 3, 2012

(87) PCT Pub. No.: WO2010/125034
PCT Pub. Date: Nov. 4, 2010

(65) Prior Publication Data
US 2012/0123363 A1  May 17, 2012

(30) Foreign Application Priority Data
May 1, 2009  (EP) .................................. 09159273

(51) Int. Cl.
*A61F 5/448*  (2006.01)
*A61M 1/00*  (2006.01)
(Continued)

(52) U.S. Cl.
CPC ................ *A61F 5/448* (2013.01); *A61B 5/01* (2013.01); *A61L 24/00* (2013.01); *A61M 1/00* (2013.01); *A61M 27/00* (2013.01)

(58) Field of Classification Search
CPC ........... A61M 1/00; A61M 27/00; A61B 5/01; A61B 5/20; A61B 17/32; A61F 5/44; A61F 9/00; A61L 2400/14
(Continued)

(56) References Cited

U.S. PATENT DOCUMENTS 4,889,534 A * 12/1989 Mohiuddin ............. A61F 5/448
604/339
5,520,670 A * 5/1996 Blum ............................ 604/338
(Continued)

FOREIGN PATENT DOCUMENTS

GB  2151482 A  7/1985
GB  2329838 A  4/1999
(Continued)

OTHER PUBLICATIONS

International Search Report for PCT/EP2020/055577, dated Jul. 2, 2010 (4 pages).
(Continued)

Primary Examiner — Tatyana Zalukaeva
Assistant Examiner — Guy K Townsend
(74) Attorney, Agent, or Firm — Levenfeld Pearlstein, LLC (57) ABSTRACT

According to an embodiment of the invention, an ostomy appliance coupling system is disclosed. The system comprises a wafer part having a rise extending away from a body surface to form a guide means and a shallow landing zone; a pouch part having a guide adapted to engage with the landing zone in a desired location relative to the guide
(Continued)

means; and an adhesive layer recessed within the guide and adapted to adhere to the landing zone.

18 Claims, 11 Drawing Sheets

(51) Int. Cl.
*A61B 5/01* (2006.01)
*A61M 27/00* (2006.01)
*A61L 24/00* (2006.01)

(58) Field of Classification Search
USPC ........ 604/317, 318, 323–327, 332, 336–339, 604/341–345, 355, 356
See application file for complete search history.

(56) References Cited

U.S. PATENT DOCUMENTS

| | | | |
|---|---|---|---|
| 6,537,261 B1* | 3/2003 | Steer | A61F 5/448 604/342 |
| 6,840,924 B2* | 1/2005 | Buglino | A61F 5/443 604/337 |
| 2006/0111682 A1* | 5/2006 | Schena | A61F 5/4407 604/334 |
| 2006/0184145 A1* | 8/2006 | Ciok et al. | 604/338 |
| 2011/0118684 A1* | 5/2011 | Nguyen-DeMary | A61F 5/448 604/344 |
| 2011/0213321 A1* | 9/2011 | Fattman | A61F 5/443 604/344 |
| 2012/0123363 A1* | 5/2012 | Grum-Schwensen | A61F 5/448 604/342 |

FOREIGN PATENT DOCUMENTS

| | | |
|---|---|---|
| JP | S6343676 A | 2/1988 |
| JP | S63150068 A | 6/1988 |
| JP | H04231045 A | 8/1992 |
| JP | 2500673 Y2 | 7/1994 |
| JP | 2582819 B2 | 2/1997 |
| JP | H11267146 A | 10/1999 |
| JP | 2000070294 A | 3/2000 |
| JP | 2001029377 A | 2/2001 |
| WO | WO-96/38106 A1 | 12/1996 |
| WO | WO-9926565 A1 | 6/1999 |
| WO | WO-2005120405 A1 | 12/2005 |
| WO | WO 2007121744 A1 * | 11/2007 ............. A61F 5/443 |

OTHER PUBLICATIONS

Written Opinion for PCT/EP2020/055577, dated Jul. 2, 2010 (5 pages).

* cited by examiner

OSTOMY APPLIANCE COUPLING SYSTEM AND AN OSTOMY APPLIANCE

REFERENCE TO RELATED APPLICATIONS

This is the U.S. national phase of International Application No. PCT/EP2010/055577, filed Apr. 27, 2010, which claims the priority benefit of European Patent Application No. 09159273.3, filed May 1, 2009, the entire disclosures of which are incorporated herein by reference.

FIELD OF THE INVENTION

The present invention relates to an ostomy appliance. More particularly, the present invention relates to a coupling system for the ostomy appliance.

DESCRIPTION OF RELATED ART

Ostomy appliances of the so-called "two-piece" type are well known. Such appliances consist essentially of an adhesive faceplate that is adhesively attached to the peristomal skin surfaces of a wearer/user and a collection pouch that is detachably connectable to the faceplate. The faceplate and pouch have alignable stoma receiving openings, and a pair of coupling devices to secure the faceplate and pouch about such openings for connecting the parts together. The advantage of such a two-piece appliance over a conventional one-piece appliance, (in which a pouch and faceplate are permanently connected) is that a number of pouches may be used successively with a single faceplate. The user of a two-piece appliance may therefore leave a faceplate adhesively attached to the skin for an extended period, without the discomfort, inconvenience, and skin irritation that frequent removal and replacement of an adhesive faceplate may involve, and simply remove a used pouch and replace it with a fresh pouch whenever needed. Further, a two-piece device allows for seeing the stoma while attaching the pouch over the faceplate.

To be effective, however, it is critical that a two-piece appliance be free of leakage problems since even slight leakage of liquid, solid, or gaseous matter could cause considerable inconvenience and embarrassment to the wearer. Much effort has been expended in the past to develop coupling systems that are reliable and not likely to be inadvertently detached in use, are nevertheless easy to assemble and disconnect at will, and do not leak even when a number of pouch rings have been successively coupled and uncoupled from a single faceplate ring. While some existing appliances come closer than others in achieving these objectives, their effectiveness in doing so has generally come at the sacrifice of one further objective—that of providing a coupling assembly of low enough profile that it does not protrude an appreciable distance from a wearer's body and does not produce conspicuous bulges through a wearer's clothing. Therefore, there exists a need for providing a low profile leakage free coupling system for ostomy appliances.

SUMMARY OF THE INVENTION

According to an embodiment of the invention, an ostomy appliance coupling system is disclosed. The system comprises a wafer part having a rise extending away from a body surface to form a guide means and a shallow landing zone; a pouch part having a guide adapted to engage with the landing zone in a desired position relative to the guide means; and an adhesive layer recessed within the guide and adapted to adhere to the landing zone.

Another embodiment of the invention discloses an ostomy appliance. The appliance comprises a wafer part having a rise extending away from a body surface to form a guide means and a shallow landing zone; a central wafer part opening in the wafer part to surround a stoma; a pouch part having a guide adapted to engage with the landing zone in a desired position relative to the guide means; a central pouch part opening in the pouch part adapted to align with the central wafer part opening; an adhesive layer recessed within the guide and adapted to adhere to the landing zone; and an ostomy pouch having an ostomy pouch opening and attached to a distal pouch surface of the pouch part such that the ostomy pouch opening is in alignment with the central pouch part opening.

Yet another embodiment of the invention discloses a method for coupling a pouch part with a wafer part of an ostomy appliance. The method comprises positioning a pouch part on a wafer part using a guide means of the wafer part and a guide of the pouch part. Thereafter, an adhesive layer, which is recessed within the guide, is adhered to a landing zone of the wafer part.

BRIEF DESCRIPTION OF THE ACCOMPANYING FIGURES

The embodiments of the invention, together with its advantages, may be best understood from the following detailed description taken in conjunction with the accompanying figures in which.

DETAILED DESCRIPTION OF THE INVENTION

The term "ostomy" is intended to be interpreted broadly and includes colostomy, urostomy, and ileostomy. The teachings of this invention may also be employed in fistula, continence care and wound care.

Figure 1:
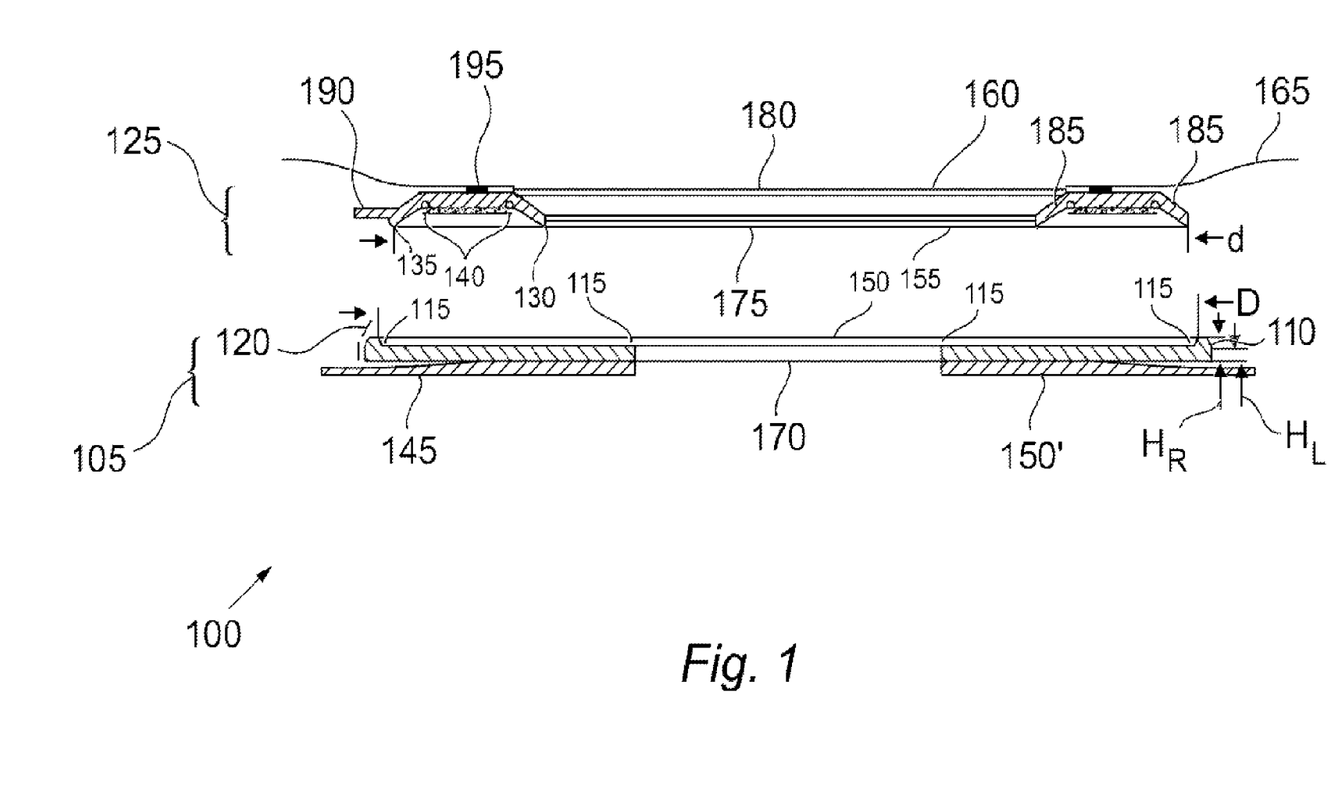
FIG. 1 illustrates a schematic cross section view of a coupling system according to an embodiment of the invention.

FIG. 1 illustrates a schematic cross section view of a low-profile coupling system 100 according to an embodiment of the invention. The coupling system 100 includes a wafer part 105 having a rise 110 extending away from a body surface to form a guide means 120 and having a shallow landing zone 115; a pouch part 125 having a guide 185 adapted to engage with the landing zone 115 in a desired position relative to the guide means 120; and an adhesive layer 140 recessed within the guide 185 and adapted to adhere to the landing zone 115.

The wafer part 105 includes a proximal wafer surface 145 and a distal wafer surface 150. The proximal wafer surface 145 refers to a side of the wafer part 105, which is in proximity to a body surface of a wearer. The distal wafer surface 150 refers to the side which is farther away from the body surface of the wearer relative to the proximal wafer surface. The proximal wafer surface 145 includes a proximal adhesive layer 150', which is used to attach the wafer part 105 to the body surface of the wearer. The pouch part 125 attaches to the distal wafer surface 150 using the disclosed low-profile coupling system 100. The flat distal wafer surface 150 of the wafer part 105 allows easy cleaning of the distal wafer surface 150 both before the pouch part 125 is positioned over the wafer part 105 and also after the pouch part 125 is separated from the wafer part 105.

As exemplified in FIG. 1, the rise 110 is away from the body surface and rises towards the pouch part 125. The rise 110 creates the guide means 120, which either surrounds or is located on the landing zone 115 depending upon whether the guide means 120 is peripheral. The pouch part 125 is positioned in relation to the guide means 120 on the landing zone 115. In FIG. 1, the guide means 120 is a structure that defines the boundary or periphery of the landing zone 115. "Shallow" in the shallow landing zone 115 refers to the relative height of the landing zone 115 with respect to the height of the guide means 120, i.e., $H_L < H_R$.

The pouch part 125 includes a proximal pouch surface 155 and distal pouch surface 160. The proximal pouch surface 155 refers to a side of the pouch part 125, which is closer to the body surface of the wearer and is placed in contact with the landing zone 115. The distal pouch surface 160 refers to the other side of the pouch part 125 to which an ostomy bag is sealed. The ostomy bag, represented by one of the walls 165 of the ostomy bag, is sealed together with the distal pouch surface 160 by any known sealing method, such as thermal welding, at 195. The proximal pouch surface 155 includes the guide 185 having an inner edge guide 130 and an outer edge guide 135. The inner edge guide 130 and outer edge guide 135 define the area of the guide. The adhesive layer 140 is recessed as a closed shaped structure between the inner edge guide 130 and the outer edge guide 135. "Inner" and "outer" in the inner edge guide 130 and outer edge guide 135 refers to the respective radial distances of the innermost and outermost edges of the guide 185 from the centre of the pouch part 125 with the inner edge guide 130 being closer to the centre of the pouch part.

The dimension of the pouch part 125 defined by the outer edge guide 135 is smaller than the dimension of the landing zone 115. In one of the embodiments, where an annular outer edge guide and an annular landing zone are employed, the diameter of the pouch part 125 defined by the outer edge guide 135 is smaller than that of the annular landing zone 115 of the wafer part 105, i.e. d<D. This allows for engaging the guide 185 with the landing zone 115 radially inwardly of the guide means 120, following which the inner edge guide 130 cooperates with the landing zone 115 to protect the adhesive layer 140 from the body waste material, when the ostomy appliance is in use.

The wafer part 105 also includes a central wafer part opening 170 to surround a stoma of the wearer, when the wafer part 105 is affixed to the body surface of the wearer.

Also, the pouch part 125 includes a central pouch part opening 175, which is adapted to align with the central wafer part opening 170, when the pouch part is positioned on the wafer part 105. The ostomy pouch 165 includes an ostomy pouch opening 180, and it is sealed to the distal pouch surface 160 such that the ostomy pouch opening 180 is in alignment with the central pouch part opening 175. The guide means 120, and guide 185 provide for proper positioning of the pouch part 125 on the wafer part 105. Such positioning includes placing the pouch part 125 on the wafer part 105 in a desired orientation and aligning the central pouch part opening 175 with the central wafer part opening 170 by locating the guide 185 so as to be substantially centered relative to the guide means 120. The desired orientation may include placing the pouch part 125 on the wafer part 105 such that the wearer may decide the direction of the ostomy pouch, which is sealed to the pouch part. In one embodiment, where an annular pouch part 125 is positioned on an annular wafer part 105, such positioning may include rotating the pouch part relative to the wafer part, such that the desired orientation, for example sideward, hanging down etc., of the ostomy bag with respect to the body of the wearer is achieved. This allows the wearer or operator to position the ostomy bag in the orientation where the ostomy bag 165 does not protrude an appreciable distance from the wearer's body and does not produce conspicuous bulges through a wearer's clothing. The wearer or operator may also position the bag in other desired orientations while in lying down position, such as during night.

The closed shaped structure of the adhesive layer 140 may be protected by a liner (not shown), which is to be removed before the positioning of the pouch part 125 on the wafer part 105. The liner may be any sheet material, which will adequately protect and be readily released from the adhesive layer 140. In use, the liner is removed from the adhesive layer 140, exposing the adhesive. The adhesive layer 140 is then placed over the wafer part 105 and secured adhesively to the landing zone 115.

The adhering of the adhesive layer 140 comprises pressing the pouch part 125 and wafer part 105 together to deflect the inner edge guide 130 and the outer edge guide 135 which are preferably flexible and to thereby adhesively attach the adhesive layer 140 to the landing zone 115 of the wafer part 105. Such deflection of these flexible parts as a result of applying pressure to the guide 185 allows the inner edge guide 130 and outer edge guide 135 to extend a sufficient distance away from one another until the adhesive layer 140, which is normally recessed within the guide 185 in an un-tensioned normal condition of the pouch part 125, makes contact with the landing zone 115. The pressure applied to the guide 185 will cause the inner and outer edge guides 130 and 135 to spread out and extend by a sufficient distance, not only for the adhesive layer 140 to make contact with the landing zone 115, but for there to be secure adhesion of the adhesive layer to the landing zone to ensure against unintended separation of the pouch part 125 from the wafer part 105.

In one embodiment, the wafer part 105 and the pouch part 125 are thin, flat and flexible. The wafer part 105 and pouch part 125 may be of thin, flexible, thermoplastic film or foam; however these parts may be composed of a porous thermoplastic film, closed cell foam or fabric. In another embodiment, the wafer part 105 and the pouch part 125 may be made up of a plastic, which allows for the bending and extension of the inner edge guide 130 and the outer edge guide 135.

The adhesive layers 140 and 150' may include a conventional pressure sensitive adhesive and a hydrocolloid.

The pouch part 125 may also include a release handle 190 to assist in overcoming the adhesion of the adhesive layer 140 to the landing zone 115 of the wafer part 105 to separate the pouch part from the wafer part, when the ostomy pouch is to be removed.

Figure 2A:
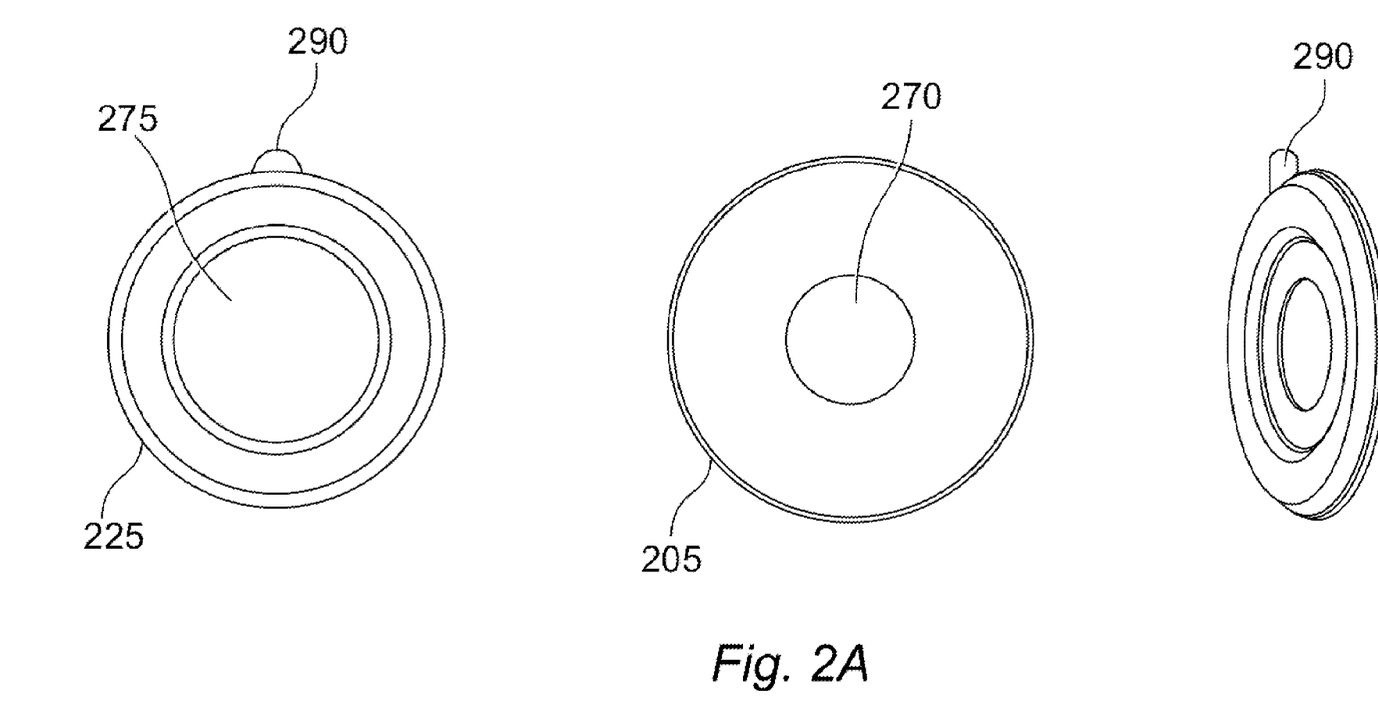
FIGS. 2A-2C illustrate a wafer part and a pouch part according to different embodiments of the invention.
Figure 2B:
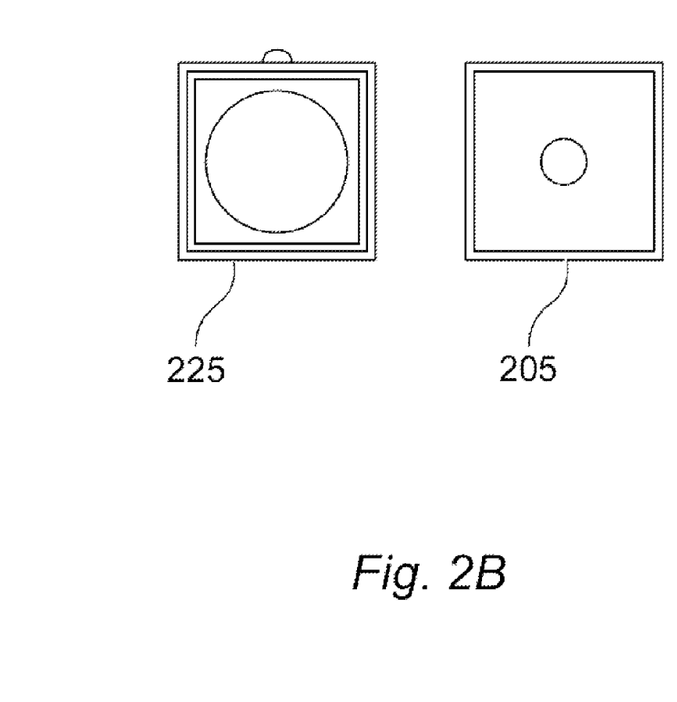
Figure 2C:
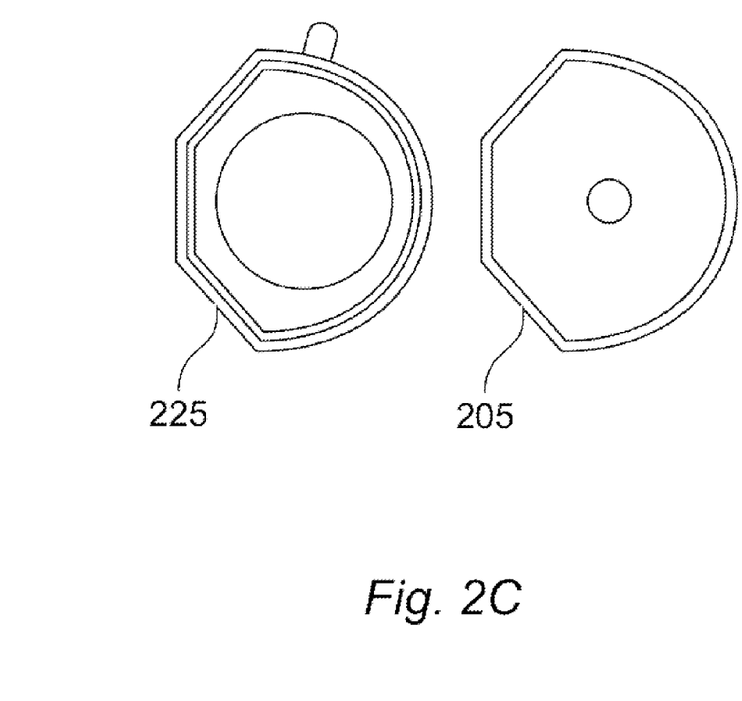

Referring now to FIG. 2A-2C, the wafer part 205 and the pouch part 225 are illustrated according to different embodiments of the invention. In one embodiment of the invention, the pouch part 225 and wafer part 205 are annular parts, as illustrated in FIG. 2A. The release handle 290 provided on the pouch part 225, the central pouch part opening 275, and the central wafer part opening 270 are also shown.

According to various other embodiments of the invention, the wafer part 205 and pouch part 225 may include any desired shaped parts, such as regular shapes, for example square parts and even irregular shapes as illustrated in FIGS. 2B, and 2C respectively.

Figures 3A, 3B, 3C, 3D, 3E, 3F:
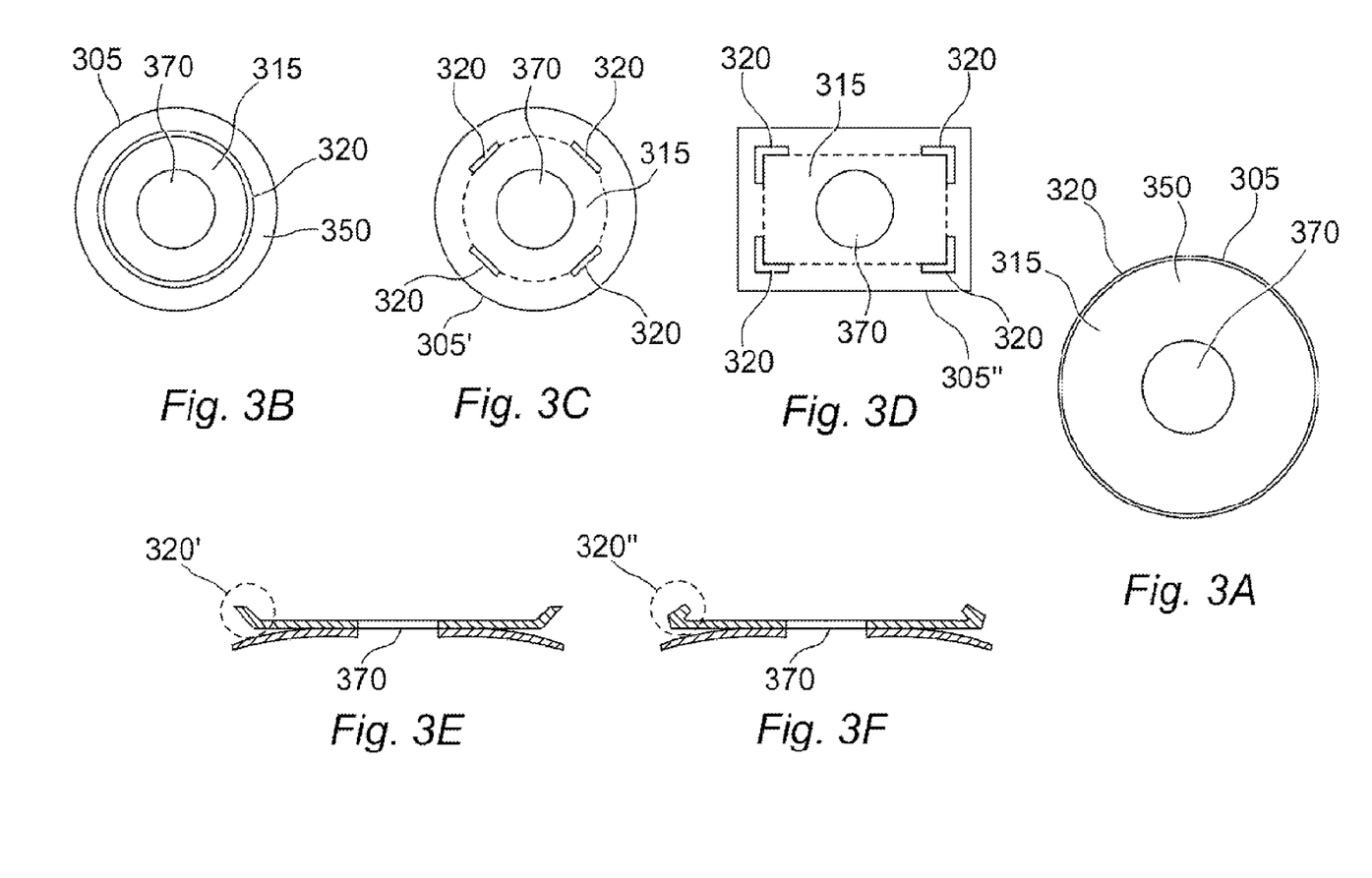
FIGS. 3A-3F illustrate a guide means according to different embodiments of the invention.

FIGS. 3A-3F illustrate the guide means 320 according to different embodiments of the invention. In one embodiment, as shown in FIG. 3A, the guide means 320 is a guide ring around the periphery of the distal wafer surface 350 of the wafer part 305. The central wafer opening 370 in the wafer part 305 and the landing zone 315 are also shown.

In another embodiment, the guide means 320 is selected from a peripheral guide means, non-peripheral guide means, continuous guide means, discrete guide means, regular shaped guide means, irregular shaped guide means, angular guide means and a combination thereof. As an illustration, FIG. 3B discloses a non-peripheral guide ring 320. In yet another embodiment, discrete non-peripheral regular shaped guide means 320 for an annular wafer part 305' and a rectangular wafer part 305" are shown in FIG. 3C and FIG. 3D respectively. The landing zone 315 is defined by the discrete guide means and a notional boundary (represented by the broken curved and straight lines, respectively) is created by the discrete guide means. Similarly, peripheral discrete guide means are also possible within the scope of this invention. In other embodiments, the guide means include angular guide means 320' and 320", which may point either outward (FIG. 3E) or inward (FIG. 3F) in addition to the vertical guide means 120, as shown in FIG. 1 of the invention. Although FIGS. 3E and 3F show peripheral outward and peripheral inward guide means 320' and 320", the invention also covers non-peripheral angular guide means and use of such guide means in different pouch parts in various embodiments of the invention.

Figures 4A, 4E:
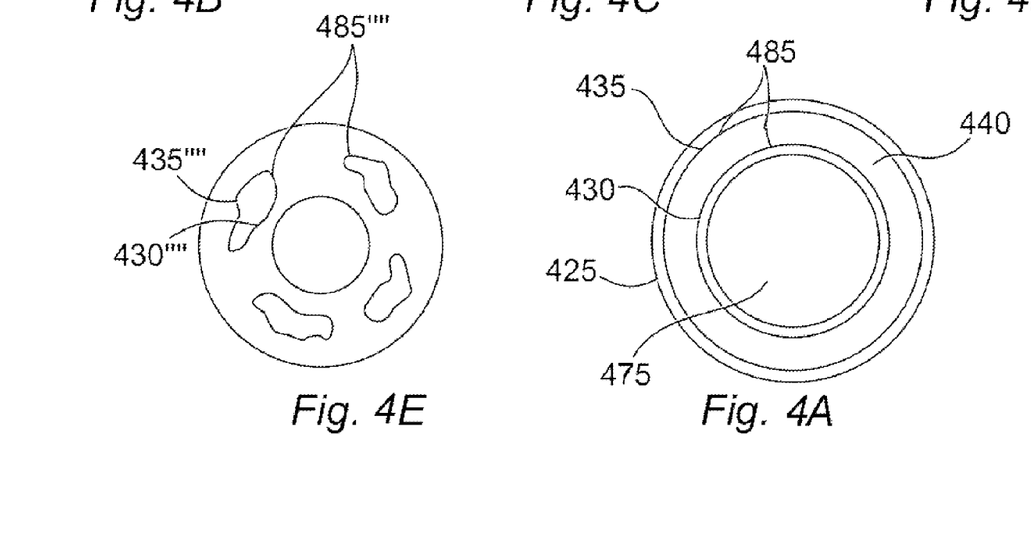
FIGS. 4A-4F illustrate a guide according to different embodiments of the invention.
Figure 4B:
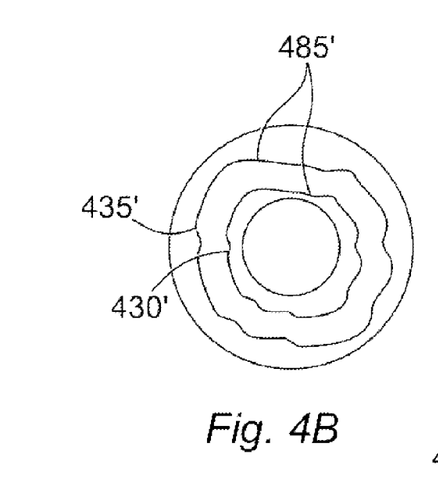
Figure 4C:
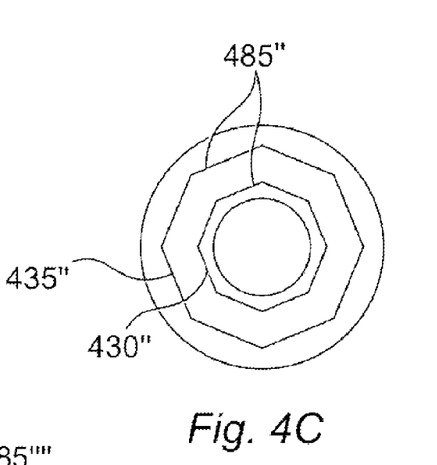
Figure 4D:
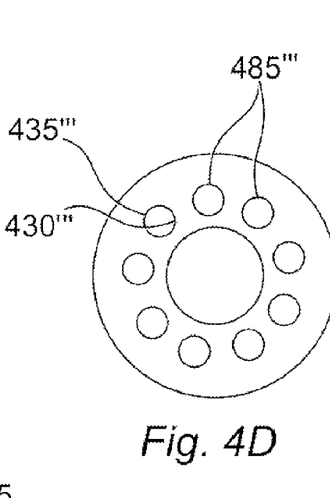
Figure 4F:
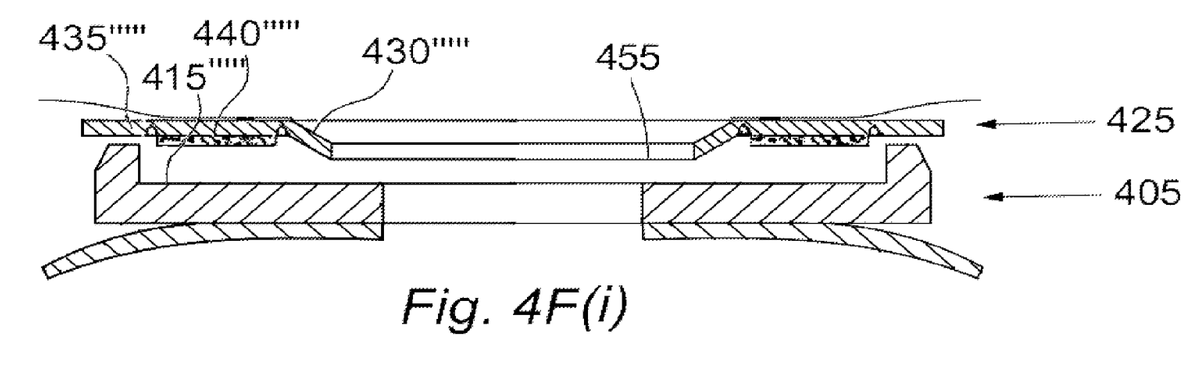

FIGS. 4A-4F illustrate a guide in the pouch part 425 according to different embodiments of the invention. The inner edge guide and outer edge guide of the guide are selected from a continuous edge guide, discrete edge guide, regular shaped edge guide, irregular shaped edge guide, peripheral edge guide, non-peripheral edge guide and a combination thereof. In one embodiment, FIG. 4A illustrates an annular guide 485 having an annular inner edge guide 430 and outer edge guide 435, forming a ring structure and defining an area in the form of a closed shaped structure within which the adhesive layer 440 is recessed. The central pouch part opening 475 is also shown.

In other embodiments, the guide includes an irregular shaped guide 485' having an irregular inner edge guide 430' and an irregular outer edge guide 435' (FIG. 4B), a regular guide 485" having regular shaped inner and outer edge guides, for example an octagonal inner edge guide 430" and an octagonal outer edge guide 435" (FIG. 4C), discrete guides 485''' each having a desired regular shape which includes an inner edge guide 430''' and an outer edge guide 435''' (FIG. 4D) or discrete guides 485'''' each having a desired irregular shape which includes an inner edge guide 430'''' and an outer edge guide 435'''' (FIG. 4E). In another embodiment, as shown in FIG. 4F(i), the guide includes an inner edge guide 430''''' and a flat outer edge guide 435'''''. When the pressure is applied, as shown in FIG. 4F(ii), the flat outer edge guide 435''''' bends to engage with the guide means and the inner edge guide 430''''' spreads out and extends a sufficient distance until the adhesive layer 440''''' makes contact with the landing zone 415''''' of the wafer part 405.

The guide may be peripheral as well as non-peripheral to the proximal pouch surface 455 of the pouch part 425. Also, FIGS. 4A-4F show a guide or guides in an annular pouch part 425, however, use of such guides in different pouch parts in various embodiments is within the scope of the invention.

Figure 5A:
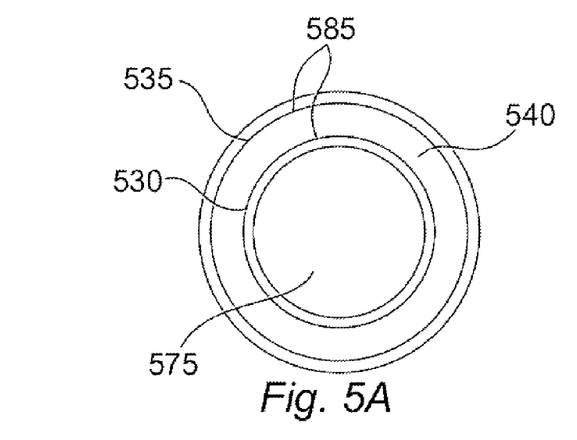
FIGS. 5A-5D illustrate a closed shaped structure of an adhesive layer according to different embodiments of the invention.
Figure 5B:
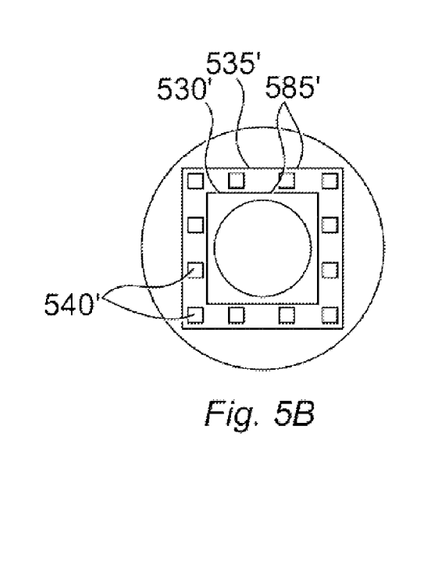

FIG. 5A-5F illustrate a closed shaped structure for an adhesive layer according to different embodiments of the invention. The closed shaped structure of the adhesive layer is selected from a continuous layer, discrete layers, regular shaped layer, irregular shaped layer and a combination thereof. In one embodiment, as shown in FIG. 5A, the closed shaped structure includes a ring like adhesive layer 540 enclosed between the annular inner edge guide 530 and the annular outer edge guide 535 of the annular guide 585. The central pouch part opening 575 is also shown.

Figures 5C, 5D:
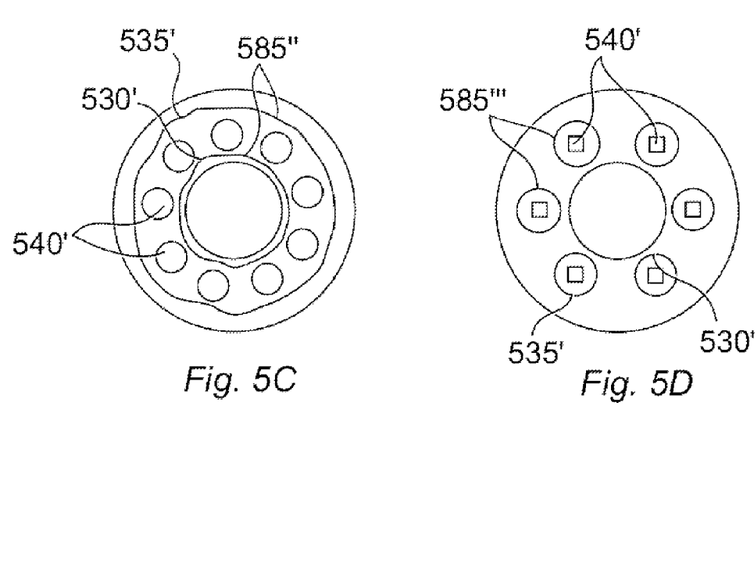

In another embodiment, the closed structure may include a desired shaped regular continuous adhesive layer, such as a rectangular continuous adhesive layer recessed within a rectangular guide, and an irregular continuous adhesive layer recessed within an irregular guide is also possible. In other embodiments, the closed structure may include discrete adhesive layers 540' recessed between the inner edge guide 530' and the outer edge guide 535' of a regular guide 585' (FIG. 5B), an irregular guide 585" (FIG. 5C), or discrete guides 585''' (FIG. 5D). A large number of combinations of continuous regular, discrete regular, continuous irregular and discrete irregular closed shaped adhesive structure in a continuous regular, discrete regular, continuous irregular and discrete irregular guide are also within the scope of this invention.

The invention is presented and described primarily for an annular wafer part having a peripheral ring based guide means and an annular pouch part having a ring based peripheral guide having an annular inner edge guide and an annular outer edge guide, between which a ring like adhesive layer is recessed. However, it is within the spirit of the invention to modify the structure or shape of any of the components of the coupling system 100 according to the description and therefore, such modifications should be considered within the scope of the invention.

Figure 6:
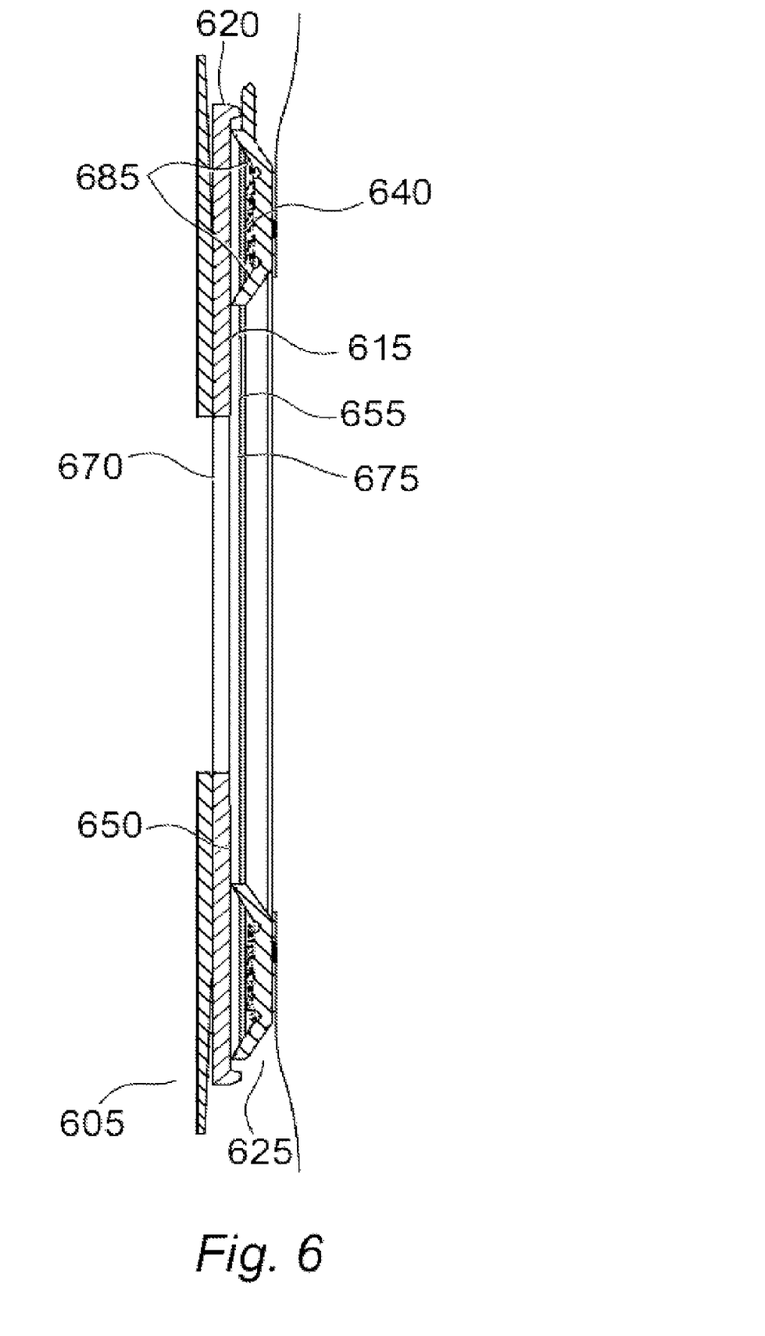
FIG. 6 illustrates a schematic cross section view of the wafer part and the pouch part when the pouch part is positioned over the wafer part according to an embodiment of the invention.

FIG. 6 illustrates a schematic cross section view of a wafer part 605 and a pouch part 625 when the pouch part is positioned over the wafer part 605 according to an embodiment of the invention. The pouch part 625 rests on top of the wafer part 605 with the proximal pouch surface 655 lying within and on the landing zone 615 of the distal wafer surface 650, as defined by the guide means 620. In this scenario, the pouch part 625 is positioned in the desired orientation and the central pouch part opening 675 is aligned with the central wafer part opening 670. This includes placing the pouch part on the wafer part such that the wearer may decide the direction of the ostomy pouch, which is sealed to the pouch part. In one embodiment, where an annular pouch part 625 is positioned on an annular wafer part 605, such positioning may include rotating the pouch part relative to the wafer part, such that the desired orientation, for example sideward, hanging down etc., of the ostomy bag with respect to the body of the wearer is achieved. This allows the wearer or operator to position the ostomy bag in the orientation where the ostomy bag does not protrude an appreciable distance from the wearer's body and does not produce conspicuous bulges through a wearer's clothing. During positioning, the adhesive layer 640 is not in contact with the landing zone 615 and is held in a non-contact position because the guide 685 creates a separation between the adhesive layer 640 and the landing zone 615. Further, during positioning, the guide 685 is not engaged with the guide means 620 and is separated by a distance.

Figure 7:
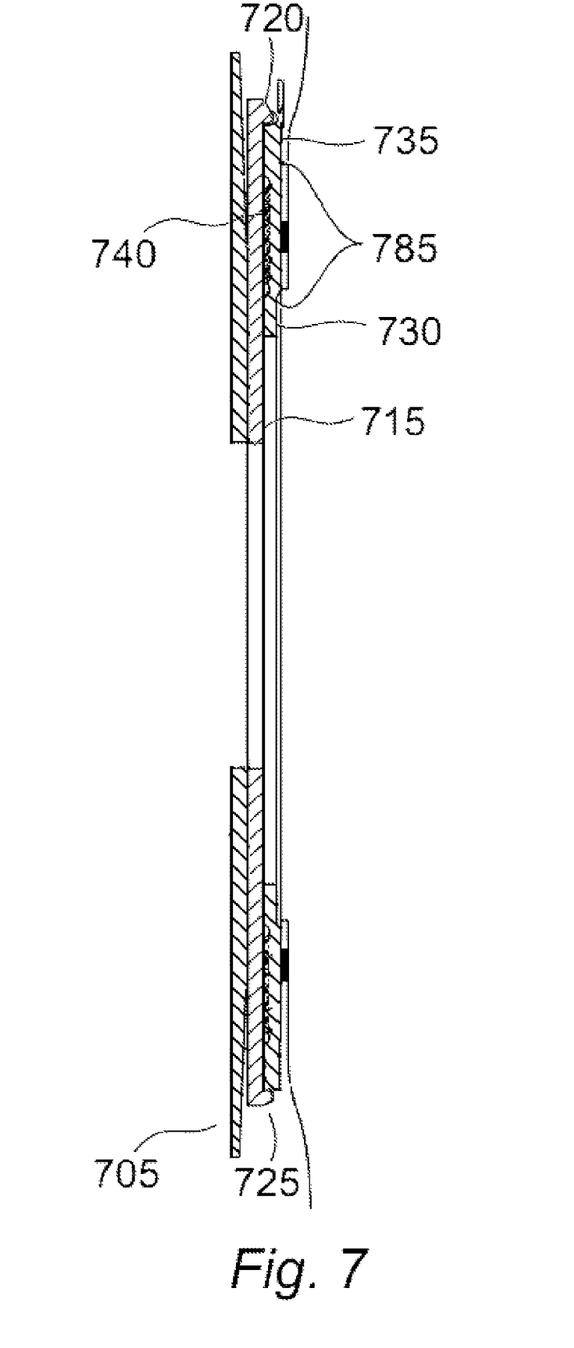
FIG. 7 illustrates a schematic cross section view of the wafer part and the pouch part when the adhesive layer is adhered to the landing zone according to an embodiment of the invention.

FIG. 7 illustrates a schematic cross section view of the wafer part 705 and the pouch part 725 with the adhesive layer 740 adhered to the landing zone 715 according to an embodiment of the invention. Once the positioning is achieved, the pouch part 725 and wafer part 705 are pressed together to deflect the inner edge guide 730 and outer edge guide 735 of the guide 785. The deflection allows the inner edge guide 730 and outer edge guide 735 to spread out and extend a sufficient distance away from one another until the adhesive layer 740, which is normally recessed within the guide 785 in an un-tensioned normal condition of the pouch part 725, makes contact with the landing zone 715 of the wafer part 705. The un-tensioned normal condition defines a situation where there is no pressure created on the adhesive layer 740 within the guide 785 which is the base before the adhesive layer is brought into contact with the landing zone 715.

After the adhesive layer 740 has been brought into contact with the landing zone 715, the deflection of the flexible inner and outer edge guides 730 and 735 causes the adhesive layer to be tensioned but the adhesion to the landing zone 715 is sufficient to maintain the pouch part 725 and the wafer part 705 firmly engaged in a leak proof manner. In the shown embodiment, the extension of the outer edge guide 735 causes the guide 785 to engage the guide means 720 as shown. In other embodiments, such as when employing discrete guide and discrete guide means, both the inner edge guide and the outer edge guide engage with the guide means and protect the adhesive layer from body waste material passing between the wafer part and pouch part of the coupling. As will be appreciated, the adhesive layer 740 is adhesively adhered to the landing zone 715 by applying pressure to the guide 785. In this state, the inner edge guide 730 and outer edge guide 735 straddle the adhesive layer 740 to protect the adhesive layer from body waste material passing through the coupling.

Figure 8:
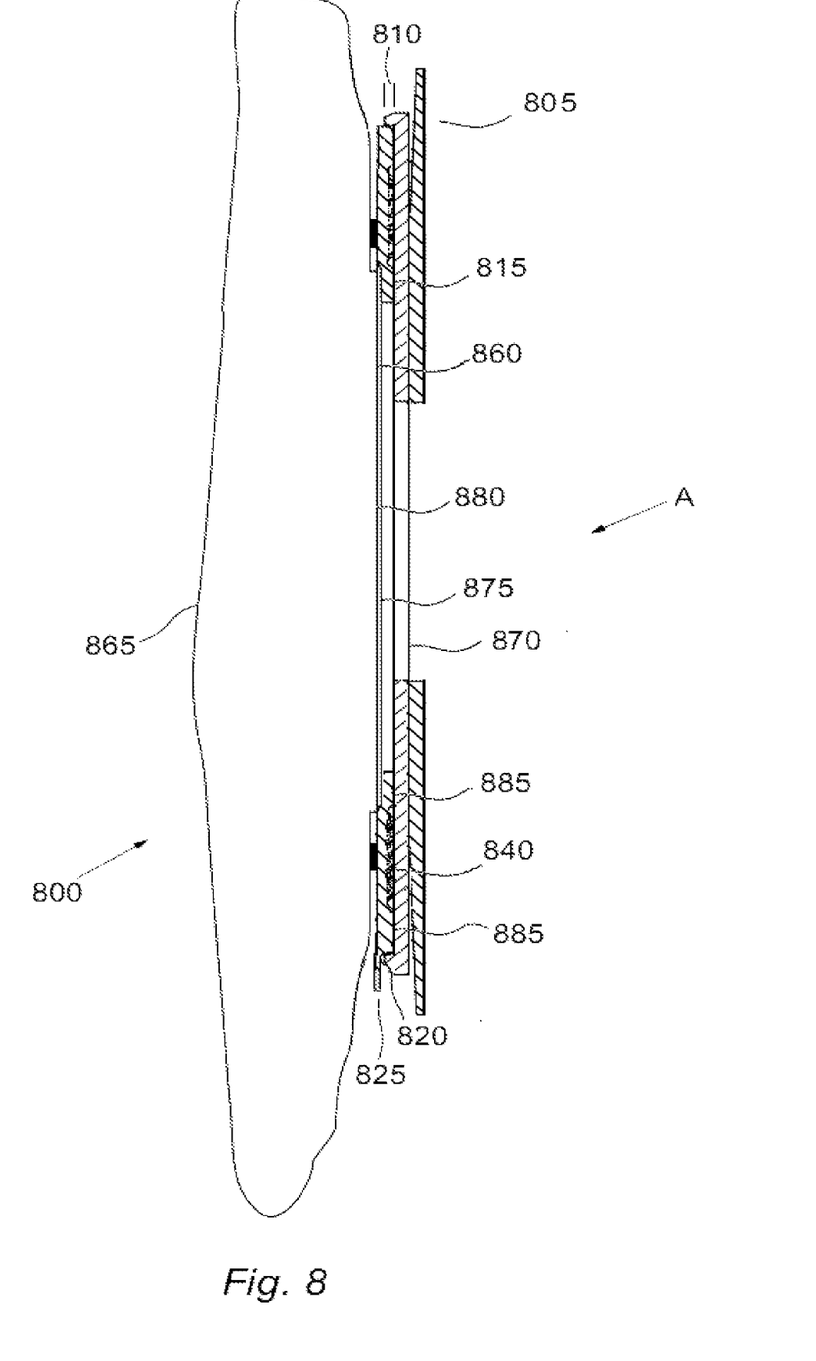
FIG. 8 illustrates an ostomy appliance according to an embodiment of the invention.

FIG. 8 illustrates an ostomy appliance 800 according to an embodiment of the invention. The ostomy appliance 800 employs the low profile coupling system, which is described earlier. The ostomy appliance 800 includes a wafer part 805 having a rise 810 extending away from a body surface to form a guide means 820 and having a shallow landing zone 815; a central wafer part opening 870 in the wafer part 805 to surround a stoma; a pouch part 825 having a guide 885 adapted to engage with the landing zone 815 in a desired position relative to the guide means 820; a central pouch part opening 875 in the pouch part 825 adapted to align with the central wafer part opening 870; an adhesive layer 840 recessed within the guide 885 and adapted to adhere to the landing zone 815; and an ostomy pouch 865 having an ostomy pouch opening 880 and attached to a distal pouch surface 860 such that the ostomy pouch opening 880 is in alignment with the central pouch part opening 875. 'A' represents the body surface of a wearer.

FIGS. 9A-9D illustrate a method for coupling a pouch part with a wafer part of an ostomy appliance. The method includes positioning the pouch part 925 on the wafer part 905 using a guide means 920 of the wafer part 905 and a guide 985 of the pouch part 925; and adhering an adhesive layer 940, recessed within a guide 985, to a landing zone 915 of the wafer part 905. The guide 985 comprises an inner edge guide 930 and an outer edge guide 935, and the adhesive layer 940 is recessed between the inner edge guide 930 and the outer edge guide 935. The method also includes adhesively affixing the wafer part 905 on to a wearer using a proximal adhesive layer 950' provided on the proximal wafer surface 945 and attaching an ostomy pouch 965 having an ostomy pouch opening 980 to the distal body side of the pouch part 925 such that the ostomy pouch opening 980 is in alignment with the central pouch part opening 975.

Figures 9A, 9B, 9C, 9D:
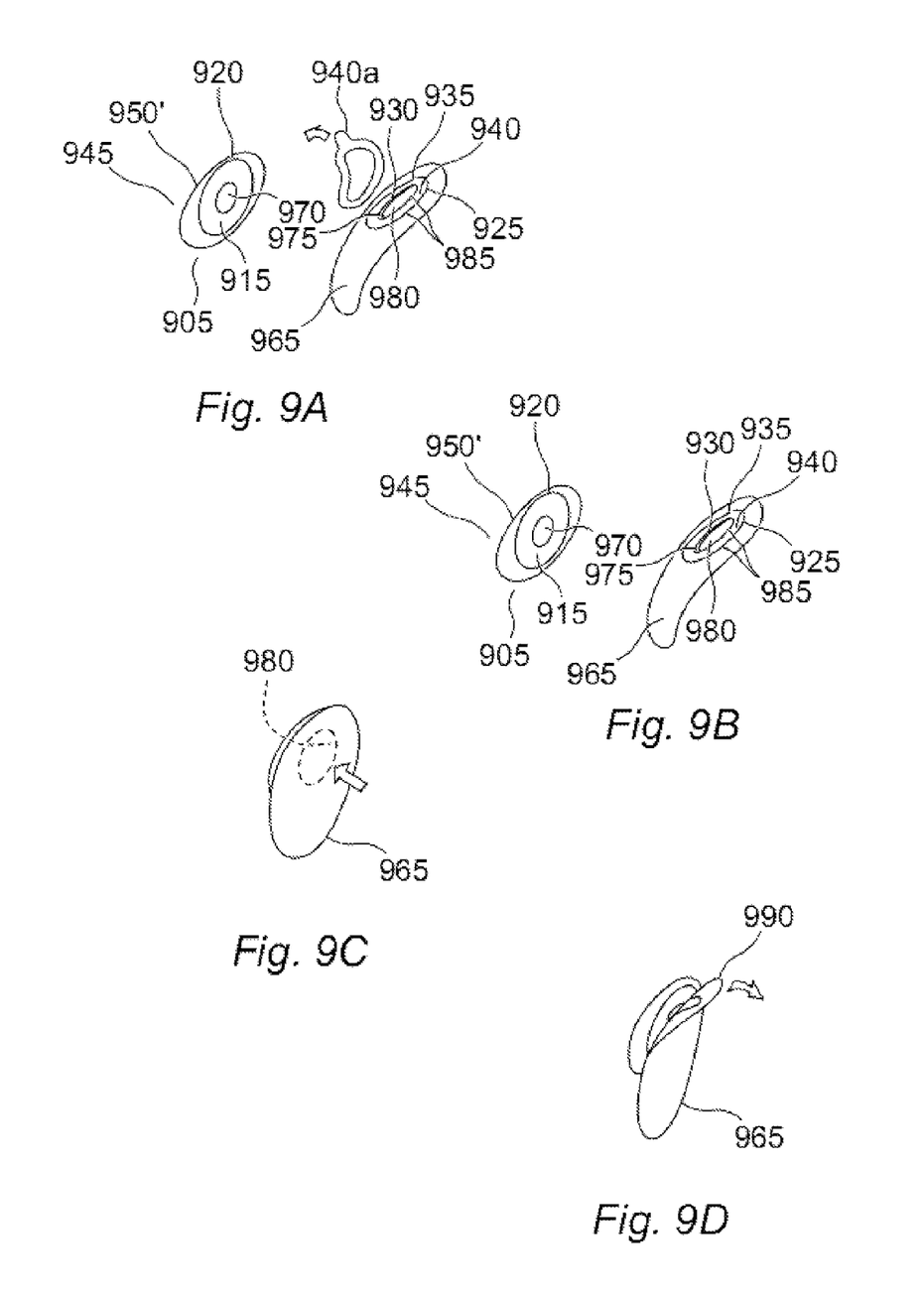
FIGS. 9A-9D illustrate a method for coupling a pouch part with a wafer part of an ostomy appliance.

Initially referring to FIG. 9A, a liner 940a is peeled off from the adhesive layer 940 before the pouch part 925 is positioned on the wafer part 905.

FIGS. 9B and 9C show the positioning and adhering of the adhesive layer 940, respectively.

The positioning includes placing the pouch part 925 on the wafer part 905 in a desired orientation and aligning a central pouch part opening 975 with a central wafer part opening 970. This includes placing the pouch part 925 on the wafer part 905 such that the wearer may decide the direction of the ostomy pouch, which is sealed to the pouch part 925. In one embodiment, where an annular pouch part 925 is positioned on an annular wafer part 905, such positioning may include rotating the pouch part 925 over the wafer part 905, such that the desired orientation, for example sideward, hanging down etc., of the ostomy bag with respect to the body of the wearer is achieved. This allows the wearer or operator to position the ostomy bag in the orientation where the ostomy bag does not protrude an appreciable distance from the wearer's body and does not produce conspicuous bulges through a wearer's clothing.

The adhering comprises pressing the pouch part 925 and wafer part 905 together to deflect the flexible inner and outer edge guides 930 and 935 and adhesively adhering the adhesive layer 940 to the landing zone 915 of the wafer part 905. Such deflection of these flexible parts as a result of applying pressure to the guide 985 allows the inner edge guide 930 and outer edge guide 935 to extend a sufficient distance away from one another until the adhesive layer 940, which is normally recessed within the guide 985 in an un-tensioned normal condition of the pouch part 925, makes contact with the landing zone 915.

FIG. 9D shows that once the ostomy pouch is to be removed from use, then the pouch part 925 may be separated from the wafer part 905 using a release handle 990 that is provided on the pouch part. This assists in overcoming the adhesion of the adhesive layer 940 of the pouch part 925 to the landing zone 915 of the wafer part 905.

It is important to note that FIGS. 1-9 illustrate specific applications and embodiments of the invention, and it is not intended to limit the scope of the present disclosure or claims to that which is presented therein. Throughout the foregoing description, for the purposes of explanation, numerous specific details, such as annular pouch part, annular wafer part, guide ring, and peripheral guide, were set forth in order to provide a thorough understanding of the invention. It will be apparent, however, to one skilled in the art that the invention may be practised without some of these specific details and by employing different embodiments in combination with one another. The underlying principles of the invention may be employed using a virtually unlimited number of different combinations.

Accordingly, the scope and spirit of the invention should be judged in terms of the claims which follow.

We claim:

1. An ostomy appliance coupling system, comprising:
   a wafer part having a wafer guide including a rise extending from a peripheral edge portion of a distal wafer surface, opposite a body-facing surface, and a landing zone defined between the rise and an inner portion of the distal wafer surface, the inner portion defining a central wafer part opening in the wafer part, the body-facing surface configured to attach to a user's skin around a stoma;
   a pouch part having a pouch guide on a proximal surface and comprising an inner edge guide and an outer edge guide, and a central pouch part opening configured to align with the central wafer part opening;
   an ostomy pouch attached to a distal surface of the pouch part and having an ostomy pouch opening aligned with the central pouch part opening; and
   an adhesive layer entirely provided on the proximal surface of the pouch guide between the inner edge guide and the outer edge guide and configured to adhere to the landing zone, and wherein the inner edge guide and the outer edge guide are configured to deflect under pressure such that the adhesive layer adheres to the landing zone to attach the ostomy pouch to the wafer part.

2. The system according to claim 1, wherein the positioning comprises placing the pouch part on the wafer part in a desired orientation and aligning the central pouch part opening with the central wafer part opening.

3. The system according to claim 1, wherein the ostomy pouch is sealed to the distal pouch surface by thermal welding.

4. The system according to claim 1, wherein: the wafer part and the pouch part are selected from annular parts and desired shaped parts; the wafer guide is selected from a peripheral guide means, non-peripheral guide means, continuous guide means, discrete guide means, regular shaped guide means, irregular shaped guide means, angular guide means and a combination thereof; the inner edge guide and outer edge guide are selected from a continuous edge guide, discrete edge guide, regular shaped edge guide, irregular shaped edge guide, peripheral edge guide, non-peripheral edge guide and a combination thereof; and the adhesive layer is selected from a continuous layer, discrete layers, regular shaped layer, irregular shaped layer and a combination thereof.

5. The system according to claim 1, wherein the wafer part and the pouch part are flat and flexible.

6. The system according to claim 1, wherein the dimension of the pouch part defined by an outer edge is smaller than the dimension of the landing zone, such as the diameter of the pouch part defined by an annular outer edge is smaller than that of the annular landing zone of the wafer part.

7. The system according to claim 1, further comprising a liner that is peeled off from the adhesive layer before the pouch part is positioned on the wafer part.

8. The system according to claim 1, wherein the inner edge guide and the outer edge guide can be deflected to extend so that the adhesive layer normally recessed between the inner edge guide and the outer edge guide in an untensioned normal condition of the pouch part may be adhesively adhered to the landing zone of the wafer part by applying a pressure.

9. The system according to claim 1, further comprising a proximal adhesive layer provided on the proximal wafer surface to adhesively fix the wafer part on to the body surface of a wearer.

10. The system according to claim 1, wherein the inner edge guide and the outer edge guide straddle the adhesive layer to protect the adhesive layer from body waste material passing between the wafer part and the pouch part of the coupling.

11. The system according to claim 1, further comprising a release handle provided on the pouch part to assist in overcoming the adhesion of the adhesive layer to the landing zone to separate the pouch part from the wafer part.

12. A method for coupling a pouch part with a wafer part of an ostomy appliance, comprising: positioning a pouch part on a wafer part using a wafer guide of the wafer part and a pouch guide of the pouch part, wherein the pouch guide includes an inner edge guide and an outer edge guide and an adhesive layer entirely provided between the inner edge guide and the outer edge guide; and adhering the adhesive layer to a landing zone of the wafer part by pressing the pouch part and the wafer part together to deflect the inner edge guide and the outer edge guide such that the adhesive layer adheres to the landing zone.

13. The method according to claim 12, further comprising peeling off a liner from the adhesive layer before the pouch part is positioned on the wafer part.

14. The method according to claim 12, wherein positioning comprises placing the pouch part on the wafer part in a desired orientation and aligning a central pouch part opening with a central wafer part opening.

15. The method according to claim 12, wherein the inner edge guide and the outer edge guide can be deflected to extend so that the adhesive layer normally recessed between the inner edge guide and the outer edge guide in an untensioned normal condition of the pouch part may be adhesively adhered to the landing zone by applying a pressure.

16. The method according to claim 12, further comprising adhesively affixing the wafer part on to a wearer using a proximal adhesive layer provided on the proximal wafer surface.

17. The method according to claim 12, further comprising attaching an ostomy pouch having an ostomy pouch opening to a distal pouch surface on the pouch part such that the ostomy pouch opening is in alignment with the central pouch part opening.

18. The method according to claim 12, further comprising separating the pouch part from the wafer part using a release handle provided on the pouch part, thereby assisting in overcoming the adhesion of the adhesive layer of the pouch part to the landing zone.

* * * * *

UNITED STATES PATENT AND TRADEMARK OFFICE
CERTIFICATE OF CORRECTION

PATENT NO. : 9,949,865 B2
APPLICATION NO. : 13/265507
DATED : April 24, 2018
INVENTOR(S) : Christen Grum-Schwensen et al.

It is certified that error appears in the above-identified patent and that said Letters Patent is hereby corrected as shown below:

On the Title Page

Column 1, Item (75), Inventors, Line 6, delete "Hombæk" and insert -- Hornbæk --, therefor.

In the Specification

Column 6, Line 2, delete "485'''" and insert -- 485'''" --, therefor.

Signed and Sealed this
Twenty-sixth Day of June, 2018

Andrei Iancu
*Director of the United States Patent and Trademark Office*